(12) United States Patent
Deflort et al.

(10) Patent No.: US 6,527,816 B2
(45) Date of Patent: Mar. 4, 2003

(54) ISOSORBIDE DERIVATIVES THAT CAN BE USED IN DETERGENT COMPOSITIONS FOR GASOLINE-TYPE FUELS

(75) Inventors: Bruno Deflort, Paris (FR); Stéphane Joly, Bougival (FR); Thierry Lacome, Garches (FR); Patrick Gateau, Maurepas (FR); Fabrice Paille, Limay (FR)

(73) Assignee: Institut Francais du Petrole, Rueil Malmaison Cedex (FR)

( * ) Notice: Subject to any disclaimer, the term of this patent is extended or adjusted under 35 U.S.C. 154(b) by 0 days.

(21) Appl. No.: 09/730,727

(22) Filed: Dec. 7, 2000

(65) Prior Publication Data

US 2002/0174596 A1 Nov. 28, 2002

(30) Foreign Application Priority Data

Dec. 8, 1999 (FR) .............................. 99 15572

(51) Int. Cl.⁷ ................................ C10L 1/18
(52) U.S. Cl. ......................... 44/351; 549/464
(58) Field of Search .................... 549/464; 44/351

(56) References Cited

U.S. PATENT DOCUMENTS

| 3,041,300 | A | * | 6/1962 | Morrison | ................... | 523/402 |
| 3,225,067 | A | * | 12/1965 | Maistre | ..................... | 549/464 |
| 4,604,102 | A | * | 8/1986 | Zaweski | ..................... | 44/326 |
| 4,770,871 | A | * | 9/1988 | Greenshields | ................ | 424/49 |

FOREIGN PATENT DOCUMENTS

| EP | 0 627 483 A1 | 12/1994 |
| EP | 0 759 435 A2 | 2/1997 |
| FR | 2 705 964 | 12/1994 |
| WO | WO 85/01956 | 5/1985 |
| WO | WO 98/44022 | 10/1998 |

* cited by examiner

*Primary Examiner*—Cephia D. Toomer
(74) *Attorney, Agent, or Firm*—Millen, White, Zelano & Branigan, P.C.

(57) ABSTRACT

Compositions that comprise at least one compound that corresponds to the general formula in which $R_1$, $R_2$, $R_3$ and $R_4$ each represent a hydrogen atom or a

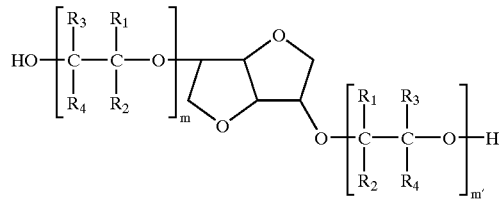

hydrocarbon radical, for example alkyl, with 1 to 30 carbon atoms, whereby at least one of $R_1$, $R_2$, $R_3$ and $R_4$ is a hydrocarbon radical, m and m' are each a number from 1 to 30, with m+m' from 4 to 60, can be prepared by reaction of the isosorbide with one or more compounds that have an epoxide group. These compositions can be used as detergent additives for gasoline-type fuels.

11 Claims, No Drawings

ISOSORBIDE DERIVATIVES THAT CAN BE USED IN DETERGENT COMPOSITIONS FOR GASOLINE-TYPE FUELS

The invention relates to new compounds that can be used by themselves or in mixtures in detergent additive compositions for fuels.

It is known that automobile engines have a tendency to form deposits on the surface of the engine elements, in particular on the carburetor orifices, the bodies of butterfly valves, fuel injectors, cylinder orifices and intake valves, because of oxidation and polymerization of various hydrocarbon-containing components of the fuel. These deposits, even when they are present only in small amounts, are often responsible for significant driving problems, such as the engine timing and poor acceleration. In addition, deposits on the engine can significantly increase the consumption of fuel and the production of pollutants. This is why the development of effective detergent additives for regulating these deposits assumes a considerable importance and was already the object of much research.

A new family of compounds that exhibit good effectiveness as additives that are intended to reduce the deposits on the injectors and on the intake valves has now been discovered.

The compounds of the invention can be defined by the following general formula (I):

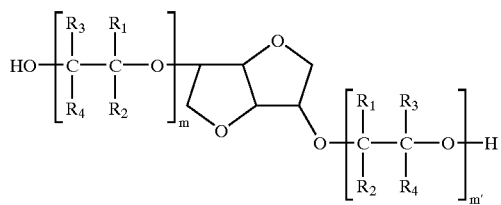

in which $R_1$, $R_2$, $R_3$, and $R_4$ each represent a hydrogen atom or a hydrocarbon radical, for example alkyl, with 1 to 30 carbon atoms, whereby at least one of $R_1$, $R_2$, $R_3$ and $R_4$ is a hydrocarbon radical; m and m' are each a number from 1 to 30, preferably 1 to 20, with m+m' from 4 to 60, preferably 5 to 30.

In the same formula (I), the concatenations

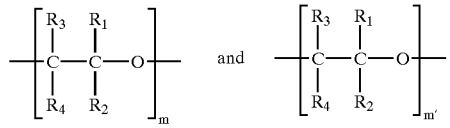

can respectively consist of patterns:

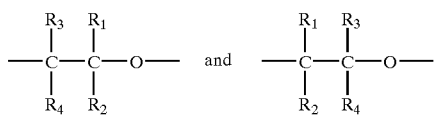

that differ from one another by the nature of $R_1$, $R_2$, $R_3$ and/or $R_4$.

The compounds of the invention generally come in the form of mixtures of compounds that differ from one another by the value of m and/or m' and/or by the nature of radicals $R_1$, $R_2$, $R_3$ and $R_4$. Rather than compounds, it is then a matter of compositions.

The synthesis of the compounds or compositions defined above can be carried out as described below.

The isosorbide of formula:

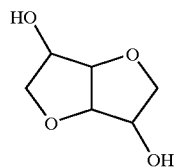

is reacted with one or more compounds that have an epoxide group, with general formula:

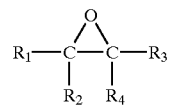

in which $R_1$, $R_2$, $R_3$, and $R_4$ each represent a hydrogen atom or a hydrocarbon radical, for example alkyl with 1 to 30 carbon atoms, whereby at least one of $R_1$, $R_2$, $R_3$ and $R_4$ is a hydrocarbon radical.

The stages of the preparation are generally as follows:

a) In a first step, the isosorbide is transformed into an alkaline metal alcoholate (for example sodium or potassium), by reaction with an alkaline hydroxide (for example soda or potash), an alkaline hydride or any other compound that can form an alcoholate with the isosorbide;

b) in a second step, the alkaline alcoholate triggers the polymerization of the epoxide(s) by opening its (their) rings; and c) in a third step, the alcoholate-termination polyether that is formed is treated by water, an acid or any other compound with mobile hydrogen, in order to transform the alcoholate terminations into alcohol groups.

Described below, by way of illustration, is a special operating procedure, whereby it is understood that the preparation of the compounds and compositions of the invention can be carried out by any other equivalent method.

The isosorbide is mixed with, for example, sodium hydride (at a rate of, for example, about 0.5% by weight). After having purged, under stirring, the reactor of the released hydrogen, an epoxide or an epoxide mixture is introduced in an amount that is calculated to obtain the desired value of m+m' at a temperature of 80 to 180° C., and the reaction mixture is kept at this temperature until the consumption of the epoxide(s) is finished. After returning to ambient temperature, the medium is diluted with an organic solvent, for example a hydrocarbon solvent, such as heptane, it is washed with water one or more times, then, after evaporation under reduced pressure of the organic phase, the desired product that corresponds to general formula (I):

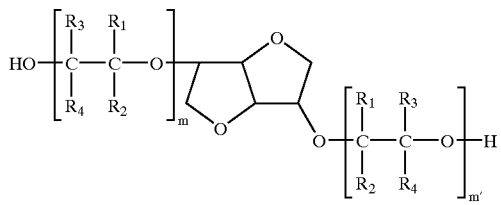

is obtained.

The compositions of the invention can be used as detergent additives in the gasoline-type fuels. In this application, they can be added to the fuels at concentrations of, for example, 20 to 5000 mg/liter. They can also be used mixed with any other detergent compound.

The following examples illustrate the invention without limiting its scope.

EXAMPLE 1

In a reactor that makes it possible to operate under pressure, equipped with a stirring system, a system for introducing reagents, a system for measuring temperature and pressure, 43.8 g (0.3 mol) of isosorbide and 0.3 g of sodium hydride are introduced. After having purged, under stirring, the reactor of the released hydrogen, 300 g (4.16 mol) of 1,2-epoxybutane is introduced. The medium is gradually brought to the temperature of 145° C., and it is kept at this temperature until the drop in pressure indicates the consumption of 1,2-epoxybutane is finished. After returning to ambient temperature, the medium is diluted with heptane, washed with 2×100 g of water, then, after evaporation under reduced pressure of the organic phase, 337 g of a clear pale yellow liquid is obtained that is soluble in gasoline and whose structure corresponds to the general formula:

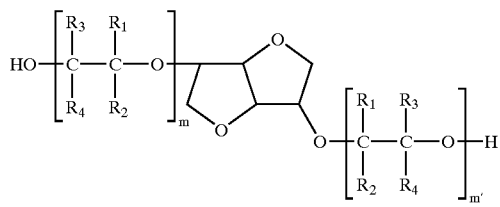

in which $R_1=R_2=R_3=H$; $R_4=-CH_2-CH_3$; and $(m+m')_{mean}=14$.

EXAMPLE 2

In a reactor that makes it possible to operate under pressure, equipped with a stirring system, a system for introducing reagents, and a system for measuring temperature and pressure, 43.8 g of isosorbide (0.3 mol) and 0.3 g of sodium hydride are introduced. After having purged, under stirring, the reactor of the released hydrogen, 420 g (5.8 mol) of 1,2-epoxybutane is introduced. The medium is gradually brought to the temperature of 145° C., and it is kept at this temperature until the drop in pressure indicates the consumption of 1,2-epoxybutane is finished. After returning to ambient temperature, the medium is diluted with heptane, washed with 2×100 g of water, then, after evaporation under reduced pressure of the organic phase, 453 g of a clear pale yellow liquid is obtained that is soluble in gasoline and whose structure corresponds to the general formula:

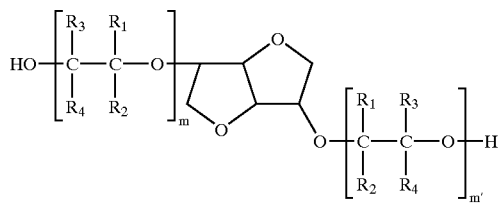

in which $R_1=R_2=R_3=H$; $R_4=-CH_2-CH_3$; and $(m+m')_{mean}=19$.

EXAMPLE 3

In a reactor that makes it possible to operate under pressure, equipped with a stirring system, a system for introducing reagents, a system for measuring temperature and pressure, 43.8 g of isosorbide (0.3 mol) and 0.3 g of sodium hydride are introduced. After having purged, under stirring, the reactor of the released hydrogen, 300 g (5.2 mol) of 1,2-epoxypropane is introduced. The medium is gradually brought to the temperature of 145° C., and it is kept at this temperature until the drop in pressure indicates that the consumption of 1,2-epoxypropane is finished. After returning to ambient temperature, the medium is diluted with heptane, washed with 2×100 g of water, then, after evaporation under reduced pressure of the organic phase, 335 g of a clear pale yellow liquid is obtained that is soluble in gasoline and whose structure corresponds to the general formula:

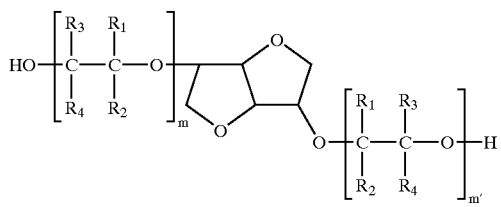

in which $R_1=R_2=R_3=H$; $R_4=-CH_3$; and $(m+m')_{mean}=17$.

EXAMPLE 4

In a reactor that makes it possible to operate under pressure, equipped with a stirring system, a system for introducing reagents, a system for measuring temperature and pressure, 43.8 g of isosorbide (0.3 mol) and 0.3 g of sodium hydride are introduced. After having purged, under stirring, the reactor of the released hydrogen, 210 g (2.9 mol) of 1,2-epoxybutane and 90 g of 1,2 epoxydodecane (0.48 mol) are introduced. The medium is gradually brought to the temperature of 145° C., and it is kept at this temperature for five hours. After returning to ambient temperature, the medium is diluted with heptane, washed with 2×100 g of water, then, after evaporation under reduced pressure of the organic phase, 333 g of a clear pale yellow liquid is obtained that is soluble in gasoline and whose structure corresponds to the general formula:

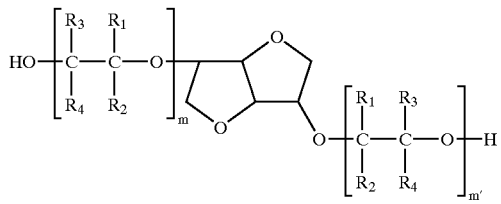

in which $R_1=R_2=R_3=H$; $R_4=-CH_2-CH_3$ or $-(CH_2)_9-CH_3$; and $(m+m')_{mean}=14.6$.

EXAMPLE 5

The products that are prepared in preceding examples 1 and 4 are evaluated as additives for their detergent properties at a concentration of 400 mg/liter in an unleaded gasoline with a "research" octane number of 96.8 and whose characteristics appear in Table 1 below.

TABLE 1

| | |
|---|---|
| Density at 15° C. | 753.9 kg/m3 |
| Reid vapor pressure | 60.2 kPa |
| Lead content | <2 mg/l |
| Distillation | |
| Starting point | 33.0° C. |
| 5% | 45.9° C. |
| 10% | 51.2° C. |
| 20% | 61.1° C. |
| 30% | 73.1° C. |
| 40% | 88.3° C. |
| 50% | 104.2° C. |
| 60% | 116.0° C. |
| 70% | 125.6° C. |
| 80% | 138.5° C. |
| 90% | 155.6° C. |
| 95% | 169.8° C. |
| End point | 189.0° C. |

The evaluation is carried out with a test on a Mercedes M102E engine according to the CEC-F-05-A-93 method. The duration of this test is 60 hours. This method makes it possible to evaluate the amount of deposits that are formed on the intake valves of the engine.

The results that appear in Table 2 show the effect of the products of the invention for reducing the deposits on the intake valves.

TABLE 2

| Additive | Content (mg/l) | Deposited Material on the Intake Valves (mg) | | | | |
|---|---|---|---|---|---|---|
| | | Valve 1 | Valve 2 | Valve 3 | Valve 4 | Mean |
| None | 0 | 241 | 275 | 272 | 312 | 275 |
| Product of Example 1 | 400 | 54 | 31 | 33 | 55 | 43 |
| Product of Example 4 | 400 | 13 | 16 | 17 | 4 | 12.5 |

What is claimed is:

1. A gasoline composition comprising gasoline and as a detergent additive, a compound of formula (I):

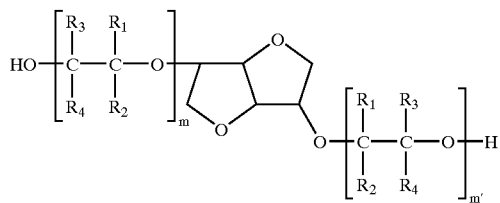

in which each of $R_1$, $R_2$, $R_3$, and $R_4$ can be the same or different and represents a hydrogen atom or a hydrocarbon radical, whereby at least one of $R_1$, $R_2$, $R_3$, and $R_4$ is a hydrocarbon radical; and m and m' are each a number from 1 to 30, with m+m' from 4 to 60, and wherein in general formula (I), hydrocarbon radicals $R_1$, $R_2$, $R_3$, and $R_4$ are alkyl radicals with one to 30 carbon atoms.

2. A gasoline composition comprising gasoline and as a detergent additive, a mixture of at least 2 compounds according to the following formula (I) that differ from one another by the values of m+m' by the nature of at least one of the radicals of $R_1$ to $R_4$,

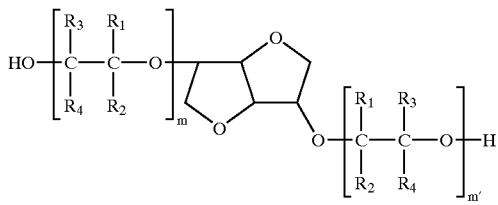

in which each of $R_1$, $R_2$, $R_3$, and $R_4$ can be the same or different and represents a hydrogen atom or a hydrocarbon radical, whereby at least one of $R_1$, $R_2$, $R_3$, and $R_4$ is a hydrocarbon radical; and m and m' are each a number from 1 to 30, with m+m' from 4 to 60.

3. A method of providing detergency to gasoline comprising adding a detergent-effective amount of a hydrocarbon-soluble compound of general formula (I):

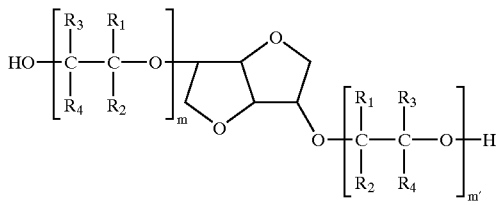

in which each of $R_1$, $R_2$, $R_3$, and $R_4$ can be the same or different and represents a hydrogen atom or a hydrocarbon radical, whereby at least one of $R_1$, $R_2$, $R_3$, and $R_4$ is a hydrocarbon radical; and m and m' are each a number from 1 to 30, with m+m' from 4 to 60.

4. A method of reducing deposits on injection and intake valves of an internal combustion engine, said method comprising operating said internal combustion engine with a gasoline composition comprising gasoline and as a detergent additive a compound of formula (I):

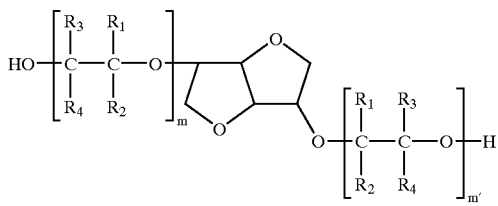

in which each of $R_1$, $R_2$, $R_3$, and $R_4$ can be the same or different and represents a hydrogen atom or a hydrocarbon radical, whereby at least one of $R_1$, $R_2$, $R_3$, and $R_4$ is a hydrocarbon radical; and m and m' are each a number from 1 to 30, with m+m' from 4 to 60.

5. A gasoline composition comprising gasoline and as a detergent additive, a hydrocarbon-soluble compound of general formula (I):

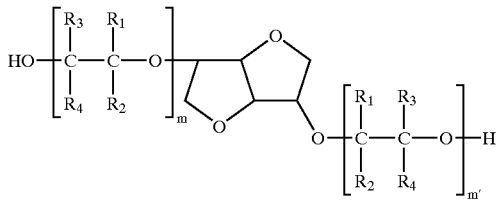

in which each of $R_1$, $R_2$, $R_3$, abd $R_4$ can be the same or different and represents a hydrocarbon atom or a hydrocarbon radical, whereby at least one of $R_1$, $R_2$, $R_3$, and $R_4$ is a hydrocarbon radical; and m and m' are each a number from 1 to 30, with m+m' from 4 to 60, with the provision that in which $R_1=R_2=R_3=H$; $R_4=$—$CH_2$—$CH_3$ or —$(CH_2)_9$—$CH_3$; and $(m+m')_{mean}=14.6$.

6. A method of reducing deposits on injections and intake valves of an internal combustion engine, said method comprising operating said internal combustion with a gasoline composition according to claim 5.

7. A gasoline composition comprising gasoline and as a detergent additive, a hydrocarbon-soluble compound of gene formula (I):

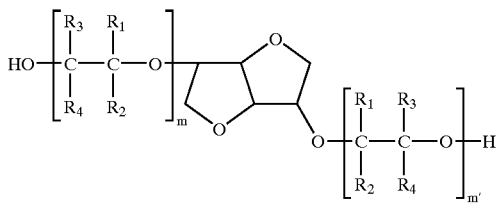

in which each of $R_1$, $R_2$, $R_3$, and $R_4$ can be the same or different and represents a hydrogen atom or a hydrocarbon radical, whereby at least one of $R_1$, $R_2$, $R_3$, and $R_4$ is a hydrocarbon radical; and m and m' are each a number from 1 to 30, with m+m' from 4 to 60.

8. A gasoline composition according to claim 7, wherein in general formula (I), the groups are defined as:

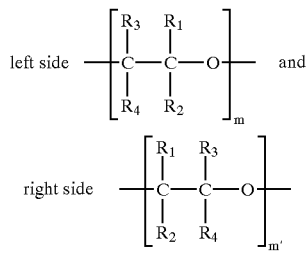

and wherein:
at least one left side $R_1$ differs from the right side $R_1$, or
at least one left side $R_2$ differs from the right side $R_2$, or
at least one left side $R_3$ differs from the right side $R_3$, or
at least one left side $R_4$ differs from the right side $R_4$.

9. A gasoline composition according to claim 7, wherein in formula (I), m and m' are each a number from 1 to 20, with m+m' from 5 to 30.

10. A process for producing a hydrocarbon-soluble compound of general formula (I):

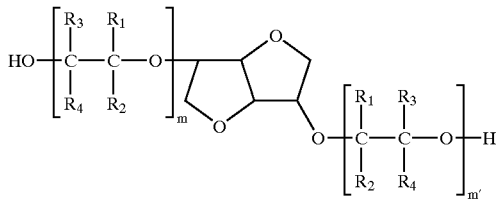

in which each of $R_1$, $R_2$, $R_3$, and $R_4$ can be the same or different and represents a hydrogen atom or a hydrocarbon radical, whereby at least one of $R_1$, $R_2$, $R_3$, and $R_4$ is a hydrocarbon radical; and m and m' are each a number from 1 to 30, with m+m' from 4 to 60, comprising, in a reactor, mixing an isosorbide with sodium hydride to form an alcoholate; purging the reactor, under stirring, to release hydrogen;

introducing an epoxide or an epoxide mixture in an amount calculated to obtain the desired value of m+m' at a temperature of 80 to 180° C.; and maintaining the reaction mixture at 80 to 180° C., until the consumption of the epoxide(s) is finished so as to form an alcoholate terminated polyether;

after returning to ambient temperature, diluting the resultant reaction mixture with an organic solvent; washing the diluted organic reaction mixture with water one or more times to transform the alcoholate groups into alcohol groups, then, under reduced pressure evaporating the resultant reaction mixture to obtain said compound of formula I, said sorbide being of the formula

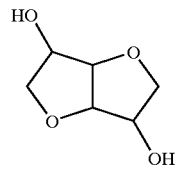

and said epoxide or epoxide mixture being of the formula

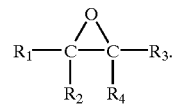

11. A hydrocarbon-soluble compound of general formula (I):

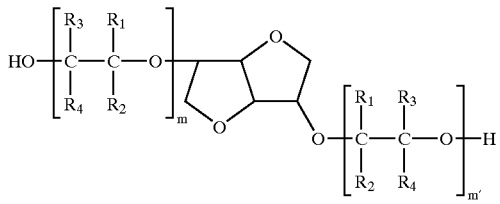

in which each of $R_1$, $R_2$, $R_3$, and $R_4$ can be the same or different and represents a hydrogen atom or a hydrocarbon radical, whereby at least one of $R_1$, $R_2$, $R_3$, and $R_4$ is a hydrocarbon radical; and m and m' are each a number from 1 to 30, with m+m' from 4 to 60, in which $R_1=R_2=R_3=H$; $R_4=$—$CH_2$—$C_3$ or —$(CH_2)_9$—$CH_3$; and $(m+m')_{mean}=14.6$.

* * * * *

UNITED STATES PATENT AND TRADEMARK OFFICE
CERTIFICATE OF CORRECTION

PATENT NO. : 6,527,816 B2
DATED : March 4, 2003
INVENTOR(S) : Bruno Deflort et al.

It is certified that error appears in the above-identified patent and that said Letters Patent is hereby corrected as shown below:

Column 7,
Line 11, reads "abd" should read -- and --
Line 25, reads "gene" should read -- general --

Signed and Sealed this

Twenty-second Day of March, 2005

JON W. DUDAS
*Director of the United States Patent and Trademark Office*